US010758660B2

(12) United States Patent
Leinfellner et al.

(10) Patent No.: US 10,758,660 B2
(45) Date of Patent: Sep. 1, 2020

(54) DIALYSIS SYSTEM WITH ARTIFICIAL INTELLIGENCE

(71) Applicant: Fresenius Medical Care Holdings, Inc., Waltham, MA (US)

(72) Inventors: Norbert Leinfellner, Livermore, CA (US); Joseph Manakkil, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 17 days.

(21) Appl. No.: 16/228,863

(22) Filed: Dec. 21, 2018

(65) Prior Publication Data

US 2020/0197592 A1 Jun. 25, 2020

(51) Int. Cl.
*A61M 1/28* (2006.01)
*B01D 61/32* (2006.01)
(Continued)

(52) U.S. Cl.
CPC .......... *A61M 1/287* (2013.01); *A61M 1/3403* (2014.02); *B01D 61/32* (2013.01);
(Continued)

(58) Field of Classification Search
CPC ................ A61M 1/287; A61M 1/3403; A61M 2205/52; A61M 2205/502; A61M 1/282; A61M 2205/6009; A61M 2205/3584; A61M 1/14; A61M 1/1601; A61M 1/1603; A61M 1/28; A61M 2205/50; A61M 2205/60; G06F 3/04847; G06F 9/451; G06F 3/0484; G06F 3/0487; B01D 61/30; B01D 61/32
(Continued)

(56) References Cited

U.S. PATENT DOCUMENTS 5,325,510 A * 6/1994 Frazier ...................... G06F 9/52
706/10
2003/0014372 A1* 1/2003 Wheeler ............. H04L 63/0823
705/71
(Continued)

FOREIGN PATENT DOCUMENTS

EP 3148607 A2 4/2017
WO WO 2015/183981 A2 12/2015

*Primary Examiner* — Joseph W Drodge
(74) *Attorney, Agent, or Firm* — Muirhead and Saturnelli, LLC

(57) ABSTRACT

Constraining adaptive optimizations of a state of an operation module of a medical device includes determining if a new state has at least one operational parameter that is outside a constraint that has been provided to the medical device in a non-repudiable manner, accepting the new state if no operational parameters are outside any of the constraints, and reverting the medical device to a previous valid state if at least one operational parameter is outside at least one of the constraints. The adaptive optimizations may be provided using artificial intelligence along with relevant inputs thereto. The medical device may be a dialysis system. Constraint data may be provided to the medical device along with a one-way hash value of the constraint data using, for example, a SHA 256 hash. The one-way hash value may be digitally signed using a private key that is part of a public/private key pair.

18 Claims, 8 Drawing Sheets

(51) Int. Cl.
    *A61M 1/34*     (2006.01)
    *G06F 3/0484*     (2013.01)
    *G06F 9/451*     (2018.01)

(52) U.S. Cl.
    CPC ..... *A61M 1/282* (2014.02); *A61M 2205/3584* (2013.01); *A61M 2205/502* (2013.01); *A61M 2205/52* (2013.01); *A61M 2205/6009* (2013.01); *G06F 3/04847* (2013.01); *G06F 9/451* (2018.02)

(58) Field of Classification Search
    USPC ...... 604/4.01, 5.01, 6.01, 6.09, 28; 210/646; 706/14, 924
    See application file for complete search history.

(56) References Cited

U.S. PATENT DOCUMENTS

| | | | | |
|---|---|---|---|---|
| 2005/0144437 | A1* | 6/2005 | Ransom | G06F 1/28 713/151 |
| 2007/0223685 | A1* | 9/2007 | Boubion | H04L 9/3231 380/2 |
| 2009/0110145 | A1* | 4/2009 | Lu | A61N 5/103 378/65 |
| 2013/0006429 | A1* | 1/2013 | Shanmugam | F02C 9/42 700/286 |
| 2013/0276780 | A1* | 10/2013 | Tobia | A61M 16/0051 128/202.22 |
| 2015/0253979 | A1* | 9/2015 | Popescu | G06F 3/0304 715/771 |
| 2016/0074582 | A1* | 3/2016 | Becker | G06F 19/3468 604/503 |
| 2017/0046729 | A1* | 2/2017 | Breslin | G06Q 30/0214 |
| 2017/0168688 | A1* | 6/2017 | Yuds | A61M 1/34 |
| 2017/0229006 | A1* | 8/2017 | Tonna | G16H 40/20 |
| 2017/0368248 | A1* | 12/2017 | Neftel | A61M 1/282 |
| 2018/0043078 | A1* | 2/2018 | Gerber | A61M 1/282 |
| 2019/0013934 | A1* | 1/2019 | Mercuri | G06F 9/542 |
| 2019/0121935 | A1* | 4/2019 | Ho | G16B 20/00 |
| 2019/0122764 | A1* | 4/2019 | Handler | A61M 16/024 |
| 2020/0074059 | A1* | 3/2020 | Beckett, Jr. | G06F 16/955 |

* cited by examiner

DIALYSIS SYSTEM WITH ARTIFICIAL INTELLIGENCE

TECHNICAL FIELD

This application relates to medical dialysis systems and more particularly to medical dialysis systems that use artificial intelligence.

BACKGROUND

Dialysis machines are known for use in the treatment of renal disease. Two types of dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, also called PD cyclers, are designed to control the entire peritoneal dialysis process so that it can be performed at home, usually overnight, without clinical staff in attendance.

Many different types of systems benefit from adaptive operation that is provided when used with artificial intelligence. In such systems, operational parameters are modified based on data inputs thereto that provide feedback to the artificial intelligence systems. For example, a speech recognition system may adapt and improve based on data input thereto that indicates successes and failures. The adaptive optimizations may be provided by artificial intelligence processing that revises operation states of the speech recognition system. Although dialysis systems could benefit from adaptive optimizations provided by artificial intelligence, such adaptions, on their own, run the risk of causing a dialysis system to not operate as originally intended, to the possible detriment of patients. In addition, since design and operation of dialysis systems are regulated by the Food and Drug Administration (FDA) in the United States (other countries have similar regulatory systems), adaptive optimizations provided by artificial intelligence may cause the system to deviate from approved design parameters in a way that is not traceable/repeatable so that there is no integrity for the state-related data of a module following adaptation.

Accordingly, it is desirable to provide a mechanism to facilitate adaptation of modules of a dialysis system using artificial intelligence in a way that maintains the dialysis system in compliance with acceptable operational parameters and regulatory requirements and provides integrity for state-related data.

SUMMARY

According to the system described herein, constraining adaptive optimizations of a state of an operation module of a medical device include determining if a new state has at least one operational parameter that is outside a constraint that has been provided to the medical device in a non-repudiable manner, accepting the new state if no operational parameters are outside any of the constraints, and reverting the medical device to a previous valid state if at least one operational parameter is outside at least one of the constraints. The adaptive optimizations may be provided using artificial intelligence along with relevant inputs to the artificial intelligence. The medical device may be a dialysis system. Constraint data may be provided to the medical device along with a one-way hash value of the constraint data. The one-way hash may be a SHA256 hash that is digitally signed. The one-way hash value may be digitally signed using a private key that is part of a public key/private key pair. The system may be provided in an initial state according to an operator of the system or a patient receiving treatment from the medical device. The operator or the patient may be detected automatically by the medical device. An operation module may provide state data to a supervisor module that determines if the new state has at least one operational parameter that is outside a constraint based on state data provided by the operation module and wherein the supervisor module reverts the operation module to a previous state if at least one operational parameter is outside a constraint. A digitally signed one way hash of the state data may be provided by the operation module.

According further to the system described herein, a non-transitory computer readable medium contains software that constrains adaptive optimizations of a state of an operation module of a medical device. The software includes executable code that determines if a new state has at least one operational parameter that is outside a constraint that has been provided to the medical device in a non-repudiable manner, executable code that accepts the new state if no operational parameters are outside any of the constraints, and executable code that reverts the medical device to a previous valid state if at least one operational parameter is outside at least one of the constraints. The adaptive optimizations may be provided using artificial intelligence along with relevant inputs to the artificial intelligence. The medical device may be a dialysis system. Constraint data may be provided to the medical device along with a one-way hash value of the constraint data. The one-way hash may be a SHA256 hash that is digitally signed. The one-way hash value may be digitally signed using a private key that is part of a public key/private key pair. The system may be provided in an initial state according to an operator of the system or a patient receiving treatment from the medical device. The operator or the patient may be detected automatically by the medical device. An operation module may provide state data to a supervisor module that determines if the new state has at least one operational parameter that is outside a constraint based on state data provided by the operation module and wherein the supervisor module reverts the operation module to a previous state if at least one operational parameter is outside a constraint. A digitally signed one way hash of the state data may be provided by the operation module.

According further to the system described herein, a dialysis system includes a dialysis machine and a control unit having a processor that executes software in a non-transitory computer readable medium. The software operates the dialysis machine and constrains adaptive optimizations of a state of the dialysis system. The software includes executable code that determines if a new state has at least one operational parameter that is outside a constraint that has been provided to the dialysis system in a non-repudiable manner, executable code that accepts the new state if no operational parameters are outside any of the constraints, and executable code that reverts the medical device to a previous valid state if at least one operational parameter is outside at least one of the constraints. The adaptive optimizations may be provided using artificial intelligence along with relevant inputs to the artificial intelligence. Constraint data may be provided to the medical device along with a one-way hash value of the constraint data and the one-way hash may be a SHA256 hash that is digitally signed. The control unit may also include an operation module and a supervisor module that receives state data from the operation module and determines if the new state has at least one operational parameter that is outside a constraint based on state data provided by the operation module. The supervisor module may revert the operation module to a previous state if at least one operational parameter is outside a constraint.

Utilization of SHA256 Hash algorithms and a supervisory/authenticator module to authenticate each AI module (with the use of a single authentication master key), prevents the applied AI from overruling a safe and effective state of the medical device, which is an important requirement. Powerful features of AI (adaptive optimization: functional, operational, and user experiences, etc.) may be used while the AI feature embedded medical device still retains a safe and effective state, consistent with FDA compliant validated states.

BRIEF DESCRIPTION OF THE DRAWINGS

Embodiments and features of the system described herein are explained with reference to the several figures of the drawings, which are briefly described as follows.

DETAILED DESCRIPTION

The system described herein provides a mechanism to constrain adaptive optimizations of operation modules provided by artificial intelligence so that the operation modules do not deviate unacceptably from validated states. A control module imposes constraints on operation modules as the operation modules adapt and change. The constraints are provided to control module in a way that prevents repudiation using a digitally signed cryptographic one-way hash. Similarly, state information and state control information is exchanged between the control module and the operation modules in a way that prevents repudiation using a digitally signed cryptographic one-way hash. In addition, state data for the operation modules may be securely saved along with a digitally signed one-way hash thereof to prevent repudiation. The one-way hash may use the SHA256 hash algorithm.

Figure 1:
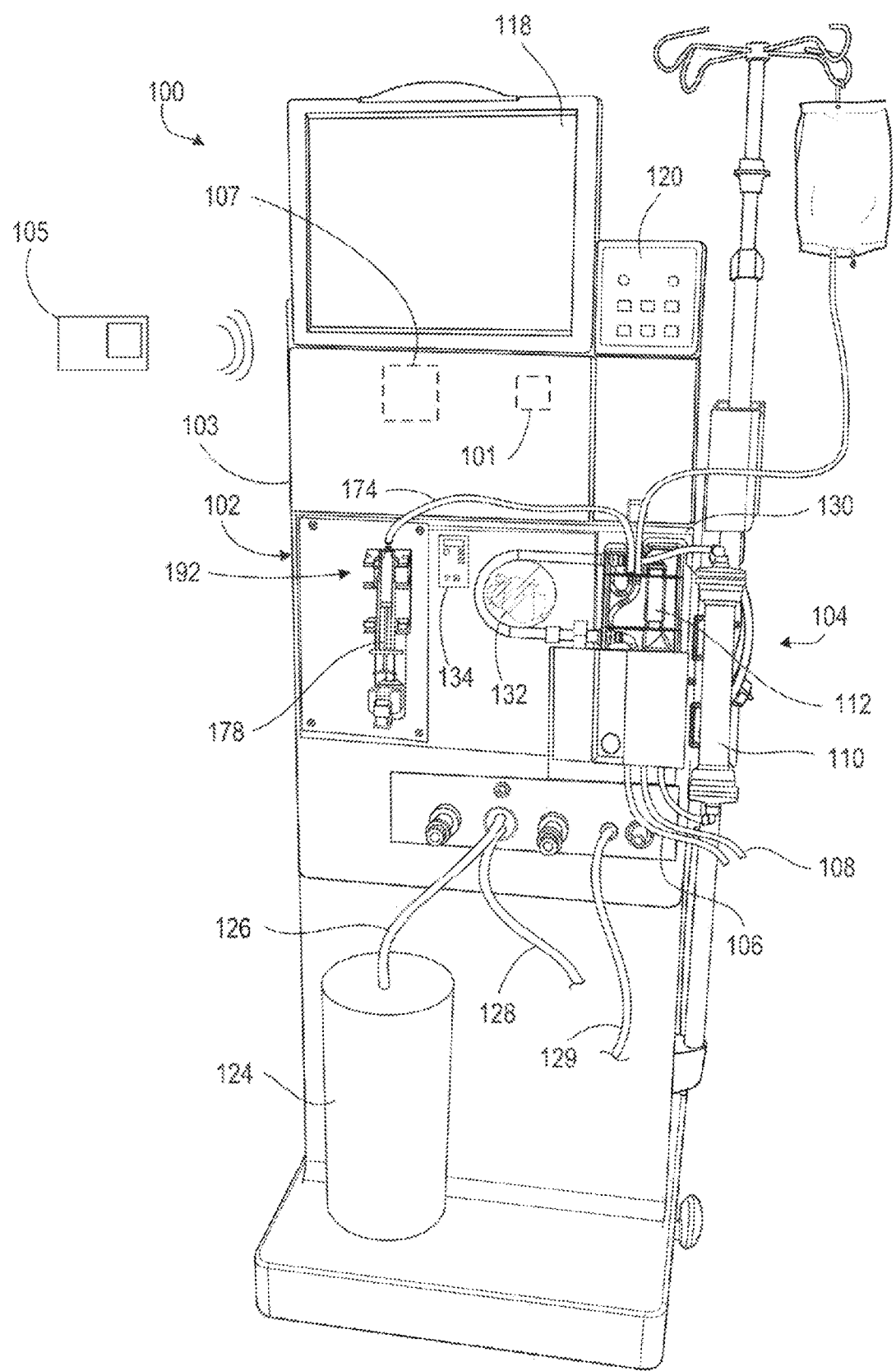
FIG. 1 shows a perspective view of a hemodialysis system according to an embodiment of the system described herein.

FIG. 1 shows a perspective view of a hemodialysis system 100 that includes a hemodialysis machine 102 connected to a disposable blood component set 104 that partially forms a blood circuit. During hemodialysis treatment, an operator connects arterial and venous patient lines 106, 108 of the blood component set 104 to a patient. The blood component set 104 includes an air release device 112, which contains a self-sealing vent assembly that allows air but does not allow liquid to pass. As a result, if blood passing through the blood circuit during treatment contains air, the air release device 112 will vent the air to atmosphere.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment sized and shaped to receive the blood component set 104. In the closed position, the door presses certain blood components of the blood component set 104 against corresponding instruments exposed on the front face of the module 130.

The operator uses a blood pump module 134 to operate the blood pump 132. The blood pump module 134 may include a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber. The controls may exist as physical buttons/switches/actuators/ etc. or wholly within a graphical user interface on a touch screen accessible display 118 or some combination thereof.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

A dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysis circuit located inside the hemodialysis machine 102. As noted above, the fresh dialysate is circulated through various dialysate lines and dialysate components, including the dialyzer 110, that form the dialysate circuit. As will be described below, as the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a control unit 101 (e.g., a processor) configured to receive signals from and transmit signals to the display 118, the control panel 120, and a communication module 107 (e.g., a near field communication (NFC) transceiver, a sensor or a camera). The control unit 101 can also communicate with a server (e.g., an Internet server), another dialysis system, or another network resource. In various examples, communication with the server may be via wireless communication over a telecommunications network, may be via a wired Ethernet connection to the server, and/or may be via physical transfer of a computer readable medium between the server and the dialysis system 100, such as using a USB drive. The control unit 101 controls operating parameters of the hemodialysis machine 102 based at least in part on signals received by the display 118, the control panel 120, and the communication module 107.

The display 118 presents a user interface that may include vital signs of a patient, operational parameters of the dialysis treatment, and controls associated with the hemodialysis process. For example, the operational parameters may include ultrafiltration parameters, blood pump rate and information associated with the dialysate, hematocrit alert levels, blood pressure alarm limits, medicine infusion parameters, etc. The display 118 may include a touch screen through which the operator may interact and control the hemodialysis machine 102. For example, the operator may input various treatment parameters associated with the hemodialysis process.

The communication module 107 is configured to detect and communicate with the short-range wireless device—for example, an ID card 105, smart card, or smartphone of an operator or a patient—when the device is within its wireless communication range. The communication between the communication module 107 and the ID card 105 is facilitated by a short-range wireless technology protocol, for example, a Bluetooth protocol or an RFID protocol, such as an NFC protocol. Because the ID card 105 is associated with an operator of the dialysis machine 102 or a patient, the communication module 107 detects information associated with the identity of the operator or patient. The communication module 107 communicates information associated with the operator or the patient to the control unit 101. In response, the control unit 101 may cause the hemodialysis machine 102 to perform an action, as described, for example, in U.S. Published Patent Application No. 2017/0168688, which is incorporated by reference herein. Similarly, when the ID card 105 is taken out of wireless communication range of the communication module 107 (e.g., the ID card 105 goes from being in wireless communication range of the communication module 107 to not being in wireless communication range of the communication module 107), the communication module 107 may send a signal to the control unit 101 indicating that the operator or patient is no longer present. In response, the control unit 101 may cause the hemodialysis machine 102 to perform an action.

The communication module 107 may also detect information associated with the identity of the operator or patient through a biometric authentication process that can include, for example, facial recognition, palm/finger print and iris recognition. The communication module may include a sensor (for example, a camera) that can take an image of the face, finger/palm or eye of the user, and use information associated with the image to identify the user. This may be achieved by comparing the information associated with the image with profile information in a database. As another alternative, the ID card 105 may be implemented as an app (or similar) on a device, such as a smartphone, tablet, etc. and the communication module 107 may detect presence of a particular operator or patient based on identification information from the app and/or identification information provided directly by the device (i.e., via an operating system of a smartphone).

The control unit 101 receives information associated with the identity of the operator or patient from the communication module 107 and compares the information with the interface configuration profiles for multiple users (operators and/or patients) stored in a database. The database may be stored on a storage device associated with the dialysis system 100 or located at an external storage device (for example a server or a storage device associated with a different dialysis system.) Based on the comparison, the control unit 101 may retrieve the interface configuration profile of the operator or patient. The specific user interface that appears on the display may be based on the retrieved interface configuration profile. For example, the operating parameters and the dialysis controls that constitute the user interface may be determined from the retrieved interface configuration profile. Additionally, identity of the operator or patient, and the identity of a supervisor of the operator may also be displayed.

The control unit 101 may communicate information associated with identity of the operator or patient and/or operational parameters of the dialysis machine 102 to a storage device or a mobile device. For example, the control unit 101 may communicate the identity of the operator or patient to a supervisor. The control unit 101 may identify the supervisor from an interface configuration profile associated with the operator. The communication, to the supervisor, may be in the form of a text message, email, social media type posting, or voicemail to a mobile device associated with the supervisor. Alternatively, or additionally, information associated with the identity of the operator or patient may be stored in a database. Storing or communicating the identity of the operator or patient and the operational parameter may allow for tracking of the dialysis process. For example, if an operator does not correctly perform the dialysis procedure, a supervisor may intervene. In another example, if an unauthorized user tries to use the system, the supervisor may undo the changes made by the unauthorized user.

The control unit 101 may be configured to add or modify a interface configuration profile. An operator or patient may register a short-range wireless device, for example an ID card 105 or a smartphone, that is associated with the operator or patient, and input the desired interface configuration profile. This can be done through a touch screen on the display 118, the control panel 120 or a kiosk that is not a part of the dialysis system 100.

The control unit 101 may be configured to detect an alarm in the hemodialysis system 100, and based on the alarm, change the user interface that appears on the display 118. The alarm may be caused when the value of an operational parameter satisfies a criteria. For example, an alarm may occur when conductivity of the dialysate is above a certain value. This may require immediate attention from a nurse, and therefore the user interface that appears on the display 118 may be changed to a form expected by and/or familiar to the nurse.

Figure 2:
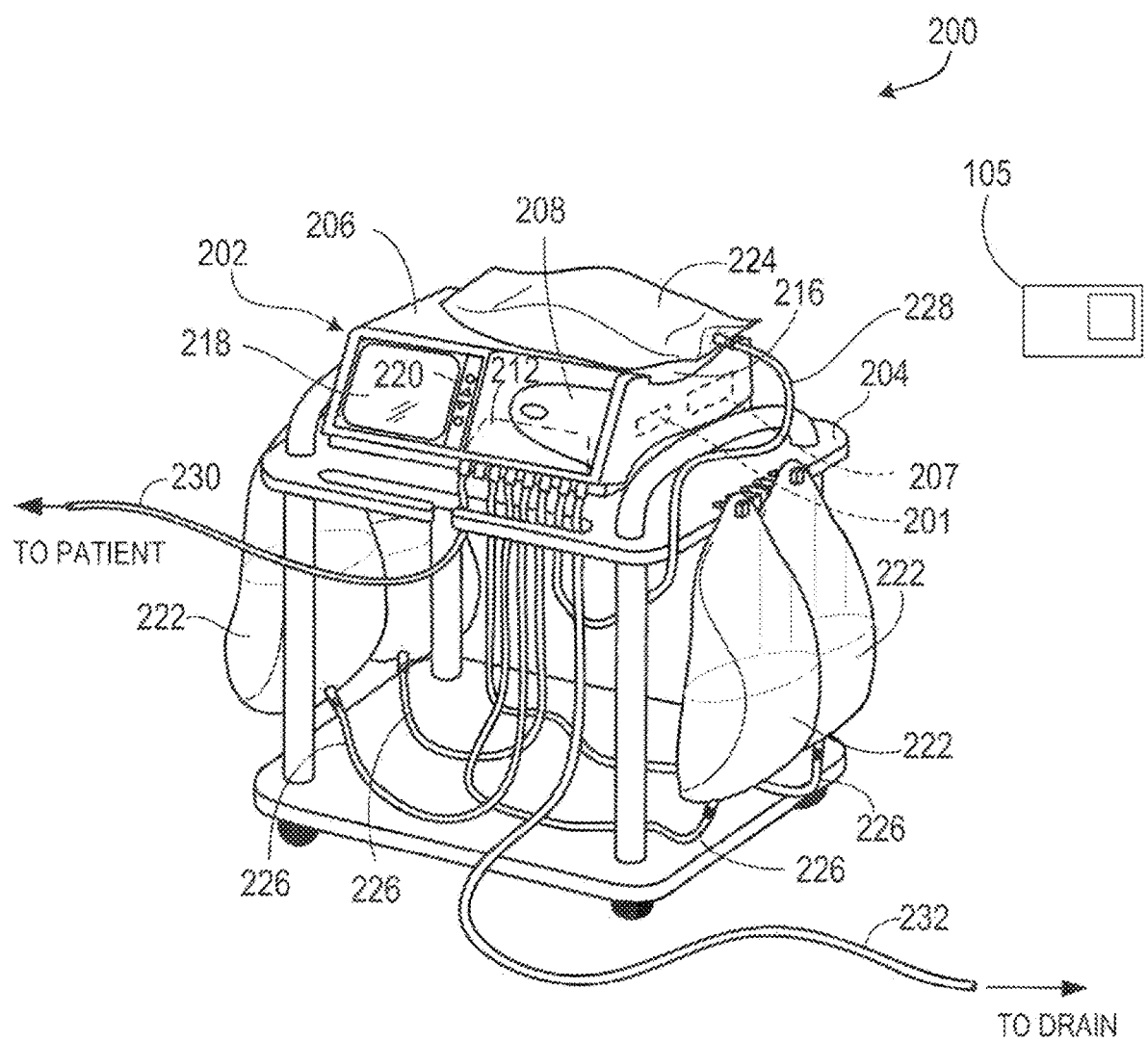
FIG. 2 shows a perspective view of a peritoneal dialysis system according to an embodiment of the system described herein.

FIG. 2 shows a perspective view of a peritoneal dialysis (PD) system 200 that includes a PD cycler (also referred to as a PD machine) 202 seated on a cart 204. The PD cycler 202 includes a housing 206, a door 208, and a cassette interface (not shown) that contacts a disposable PD cassette 212 when the cassette 212 is disposed within a cassette compartment formed between the cassette interface and the closed door 208. A heater tray 216 is positioned on top of the housing 206. The heater tray 216 is sized and shaped to accommodate a bag of dialysate (e.g., a 5 liter bag of dialysate). The PD cycler 202 also includes a display 118 and additional control panel 220 that can be operated by a user (e.g., a patient) to allow, for example, set-up, initiation, and/or termination of a PD treatment.

Dialysate bags 222 are suspended from fingers on the sides of the cart 204, and a heater bag 224 is positioned in the heater tray 216. The dialysate bags 222 and the heater bag 224 are connected to the cassette 212 via dialysate bag lines 226 and a heater bag line 228, respectively. The dialysate bag lines 226 may be used to pass dialysate from dialysate bags 222 to the cassette 212 during use, and the heater bag line 228 may be used to pass dialysate back and forth between the cassette 212 and the heater bag 224 during use. In addition, a patient line 230 and a drain line 232 are connected to the cassette 212. The patient line 230 may be connected to a patient's abdomen via a catheter and may be used to pass dialysate back and forth between the cassette 212 and the patient's peritoneal cavity during use. The drain line 232 may be connected to a drain or drain receptacle and may be used to pass dialysate from the cassette 212 to the drain or drain receptacle during use. The various components that pass dialysate form a dialysate circuit.

The PD system 200, like the hemodialysis system 100, includes a control unit 201, a display 218 and a communication module 207 that communicate with one another, and with a short-range wireless device (for example, the ID card 105 or a smartphone). Similar to the hemodialysis system 100, the PD system 200, using components such as the control unit 201 and the communication module 207, may detect information associated with the identity of an operator or patient, and change the user interface that appears on the display 218 based on an interface configuration profile. The PD system 200 allows an operator or patient to add or modify the interface configuration profile that may be stored in a storage device associated with the PD system 200, or an external storage device (for example, a server). Furthermore, the control unit 201 of the PD system 200 may change the user interface that appears on the display 218 based on an alarm in the PD system 200.

Figure 3:
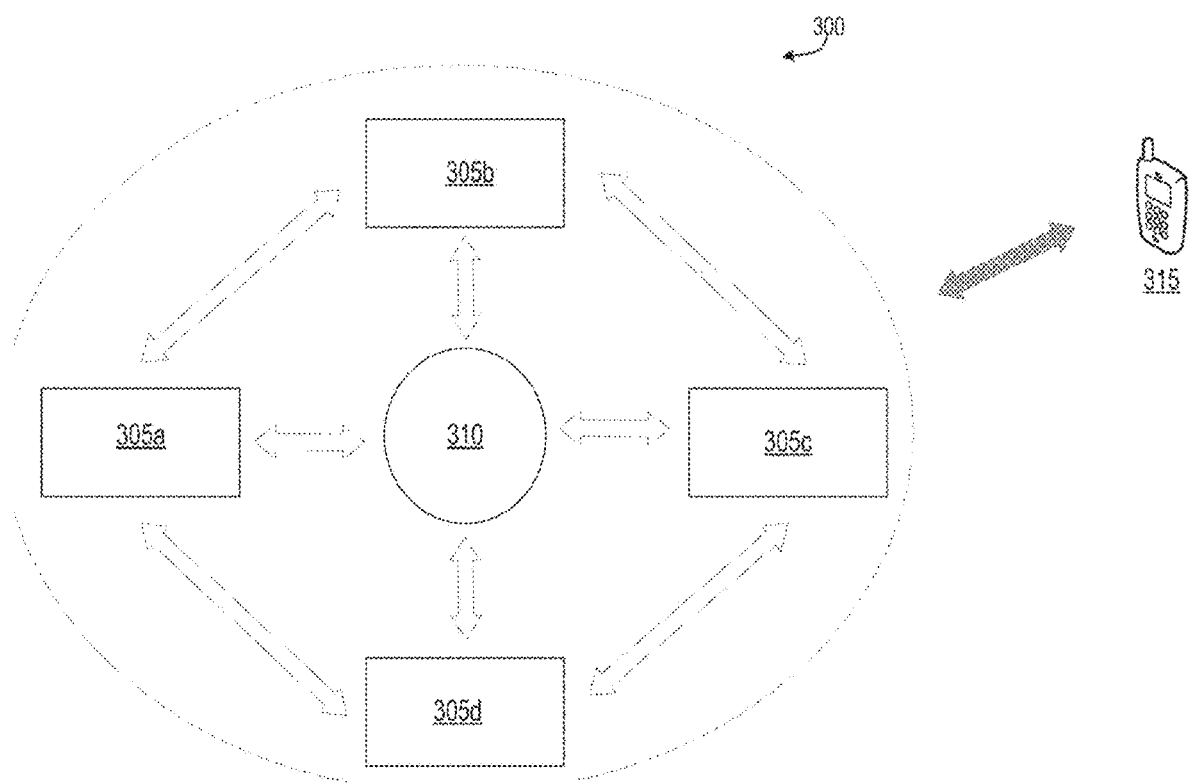
FIG. 3 shows a facility comprising plurality of dialysis systems according to an embodiment of the system described herein.

FIG. 3 shows an example of a facility 300 that includes a plurality of dialysis systems 305a-305d and a central server 310. The dialysis systems 305a-305d may communicate with each other and with the central server 310. In an implementation, the database of interface configuration profiles may be stored in the central server 310. When a dialysis system, for example the dialysis system 305a, detects a particular operator or patient, the dialysis system 305a may retrieve the interface configuration profile associated with the operator or patient from the database stored in the server. The dialysis system 305a may also add or alter a interface configuration profile of the database stored in the server. When an operator, who has been working on a first dialysis system (for example, the system 305a), is detected by another dialysis system (for example, the system 305b), the user interface of the display of the second dialysis system may be reconfigured based on the interface configuration profile of the operator. In addition, the operator may be logged out from the first dialysis system. When a dialysis system detects a particular operator or patient, information associated with identity of the operator or patient may be transmitted to an external device, for example, to a cell phone 315 or to the central server 310 or both. Additionally, data associated with the operational parameters and control of the dialysis system may also be transmitted to an external device or the central server or both.

In addition to modifying the display and initializing operational parameters based on identifying the operator or patient, the system described herein may intelligently adapt operation of modules of the dialysis systems 100, 200 based on input data provided thereto. The operational parameters that may be adapted include the displays 118, 218 as well as the rate of the dialysate and/or blood flow motor(s), the temperature of the heater tray 216, data sampling rates, alarm limits, etc. Input data that is used to adapt the operational parameters includes dialysate flow rate, blood flow rate (for hemodialysis system 100), transmembrane pressure, fluid clarity (for PD system 200), fluid temperature, fluid conductivity, air detection, blood O2 levels (for hemodialysis system 100), sodium content, and patient information such as patient blood pressure, patient temperature, other patient parameters, and possibly including responses to patient/operator queries that may be answered on one of the displays 118, 218. At least some of the input data collection may be automated (e.g., fluid flow rate) while other data may be input manually by a user (operator or patient).

Figure 4:
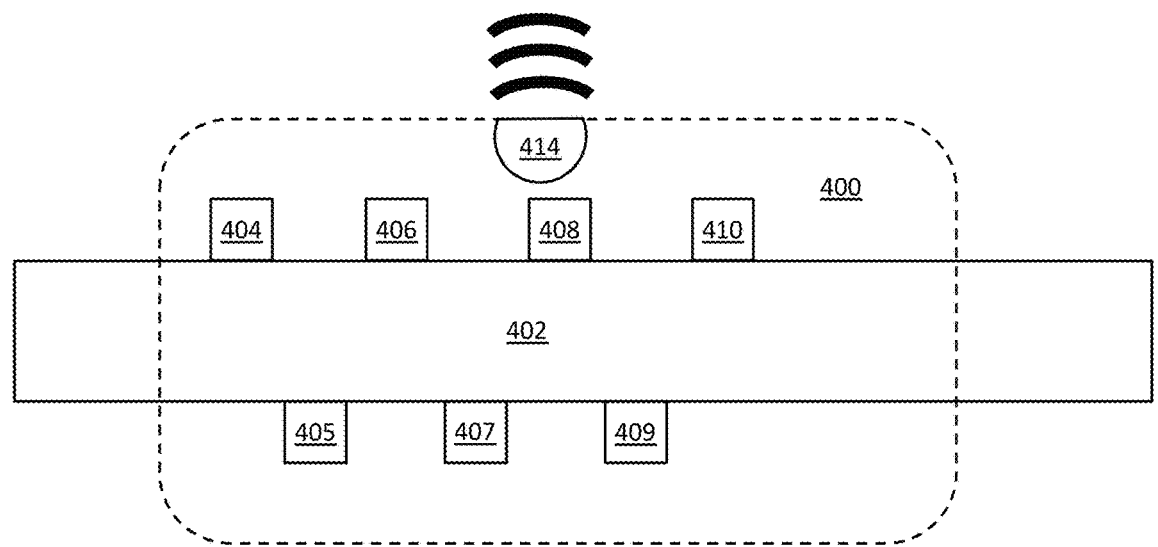
FIG. 4 shows a sensor assembly for a dialysis system according to an embodiment of the system described herein.

Referring to FIG. 4, a sensor assembly 400 includes a flow tube 402 that is connected at both ends thereof to a patient line such as one of the lines 106, 108, 230, discussed above (not shown in FIG. 4). Blood from the patient (in the case of the hemodialysis machine 100) or dialysate fluid (in the case of the PD machine 200) passes through the flow tube 402 to enter and/or leave the patient. The sensor assembly 400 includes a clarity sensor 404, an IR temperature sensor 405, a conductivity sensor 406, a flow sensor 407, a contact temperature sensor 408, an air detector 409, and a pressure sensor 410. The clarity sensor 404 measures cloudiness of fluid from the patient passing through the flow tube 402. The IR temperature sensor 405 measures temperature of fluid passing through the flow tube 402 using IR light and an IR transmissive window (not shown) placed in a portion of the flow tube 402 proximal to the sensor 405. The conductivity sensor 406 measure electrical conductivity of fluid passing through the flow tube 402, which may be a useful indication of chemical composition of the fluid, such as a concentration of salts in dialysate fluid passing from the PD cycler 202 to the patient. The contact temperature sensor 408 may measure temperature of fluid passing through the flow tube 402 using, for example, conventional temperature contact sensors and possibly having a highly thermally conductive material in a corresponding portion of the flow tube 402. The flow sensor 407 measures flow rate of fluid passing through the flow tube 402. The sensor assembly 400 may receive power using any appropriate wired or wireless mechanism.

In some embodiments, the dialysis systems 100, 200 may communicate with one or more of the sensors 404-410 using wires (not shown) coupled to the sensors 404-410. The wires may directly connect the one or more of the sensors 404-410 to the dialysis systems 100, 200. Alternatively, the wires may connect to a wired communication module (not shown) that provides a multiplexed connection to the dialysis systems 100, 200, possibly via a network. Alternatively still, the sensor assembly 400 may include a wireless communication device 414 that provides wireless communication between each of the sensors 404-410 and the dialysis systems 100, 200. Any appropriate wireless communication protocol may be used, including a connection through a secure Internet gateway to connect to a network that communicates with both the wireless communication device 414 and the dialysis systems 100, 200. The connection, network and data transmissions among components, both local and external, may be controlled and/or otherwise incorporated into a system that facilitates such functions with appropriate network infrastructure, and which may, in some implementations, be referred to as a connected health system. For further descriptions of systems for securely connecting, pairing and/or monitoring medical devices, such as in a connected health system, reference is made to US Pub. No. 20160206800 entitled "Remote Monitoring Interface Device and Mobile Application for Medical Devices" to Tanenbaum et al., U.S. Pat. No. 9,800,663 entitled "Associating Dialysis Accessories Using Near Field Communication" to Arrizza, US Pub. No. 20170087290 entitled "Short-Range Wireless Communication for a Dialysis System" to Medina et al., US Pub. No. 20170076069 entitled "Secure Network-Based System for Communication of Clinical Data" to Moissl et al., and U.S. Pat. No. 9,178,891 entitled "Remote Control of Dialysis Machines" to Wang et al., the disclosures of all of which are hereby incorporated by reference.

Figure 5:
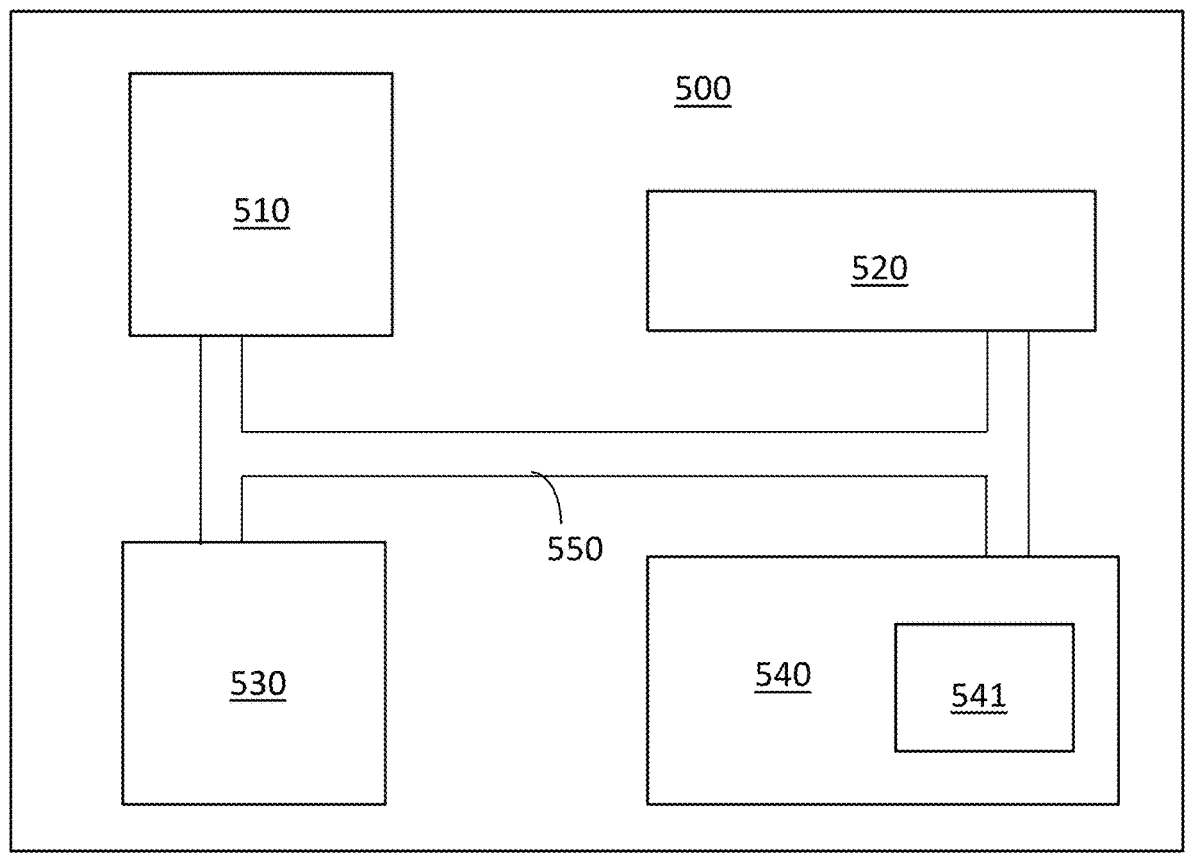
FIG. 5 shows an example of a computer system according to an embodiment of the system described herein.

Referring to FIG. 5, a block diagram shows a computer system 500 that may be used to implement the control unit 101 or the control unit 201. The system 500 includes a processor 510, a memory 520, a storage device 530, and an input/output interface 540. Each of the components 510, 520, 530, 540 may be interconnected, for example, using a system bus 550. The processor 510 is capable of processing instructions for execution within the system 500. The processor 510 may be a single-threaded processor, a multi-threaded processor, or a quantum computer. The processor 510 is capable of processing instructions stored in the memory 520 and/or on the storage device 530. The processor 510 may execute operations such as receiving signals from the sensor assembly 400, comparing data based on the signals to stored data, e.g., data stored in a look-up table of temperature values and, as described in more detail elsewhere herein, adapting operation of modules of the dialysis systems 100, 200 based on input data. In some embodiments, some or all components of the computer system may be implemented using a sealed programmable gate array (SPGA).

The memory 520 stores information within the system 500. In some implementations, the memory 520 is a computer-readable medium. The memory 520 can, for example, be a volatile memory unit or a non-volatile memory unit. The storage device 530 is capable of providing mass storage for the system 500. In some implementations, the storage device 530 is a non-transitory computer-readable medium. The storage device 530 may include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network.

The input/output interface 540 provides input/output operations for the system 500. In some implementations, the input/output interface 540 includes one or more of network interface devices (e.g., an Ethernet card), a serial communication device (e.g., an RS-232 I/O port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and the display devices 118/218, the sensor unit 400, etc. In some implementations, mobile computing devices, mobile communication devices, and other devices are used.

In some implementations, the input/output interface 540 includes at least one analog-to-digital converter 541. An analog-to-digital converter converts analog signals to digital signals, e.g., digital signals suitable for processing by the processor 500. In some implementations, one or more sensing elements (e.g., the communication module 107 shown in FIG. 1 or the communication module 207 shown in FIG. 2 or the sensor unit 400) are in communication with the analog-to-digital converter 541. In some implementations, the system 500 is a microcontroller. A microcontroller is a device that contains multiple elements of a computer system in a single electronics package. For example, the single electronics package could contain the processor 510, the memory 520, the storage device 530, and the input/output interfaces 540.

The system described herein uses artificial intelligence to allow modules of the dialysis systems 100, 200 to adapt operation thereof based on inputs (feedback). For example, the system may be used to optimize dialyzer transfer efficiently by altering blood and dialysate flow rates and measuring the resulting diffusive clearance at each iteration. Any appropriate artificial intelligence mechanism may be used, such as neural networks.

Figure 6:
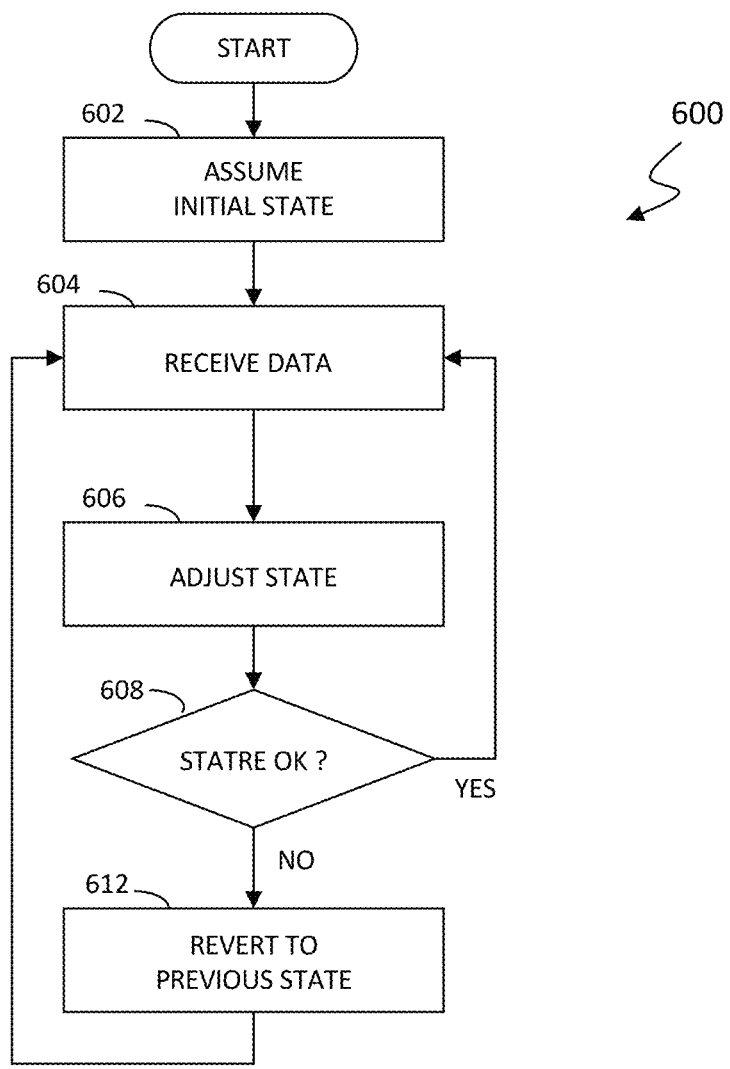
FIG. 6 is a flow diagram illustrating processing performed in connection with an operation module changing state according to an embodiment of the system described herein.

Referring to FIG. 6, a flow diagram 600 illustrates steps performed in connection with a module adapting using artificial intelligence. The processing illustrated by the flow diagram 600 may be performed by the computer system 500, described elsewhere herein, or by another processing system (not shown) that is provided either internally to one of the systems 100, 200, or externally thereto. In addition, adaptive optimizations provided by processing illustrated by the flow diagram 600 may be provided on a per patient basis, a per operator basis, for the entire device, or any other appropriate grouping. That is, the adaptation processing illustrated by the flow diagram 600 may be performed for each patient, so that the adaptive optimizations are individualized for each patient, for each operator so that the adaptive optimizations are individualized for each operator, for the entire device so that the adaptive optimizations are provide for the entire device and thus equally applied to each patient and each operator, or some other appropriate grouping. Operation modules of the system that may be adapted include operator user interface interactions with the system, optimization auto calibration functions, automatic system noise reduction and compensation (electrical and mechanical), data transport optimization, optimizing total time of dialysis and changeover, hardware and software monitoring, housekeeping, fault monitoring, and related response management, diagnostics, optimizing field service responses, etc. Generally, any operational aspect of the system may be adapted using artificial intelligence.

Processing for the flow diagram 600 begins at a first step 602 where the system is set to an initial state. The initial state may be determined at the time of manufacture or may be otherwise input to the system by a supervisor module (discussed in more detail elsewhere herein) or some other external source. For example, the initial state may include an initial value for blood flow rate and an initial value for dialysate flow rate. In some cases the initial state may be based on the specific operator and/or patient, which may be detected automatically, as described elsewhere herein. Following the step 602 is a step 604 where inputs are provided to the system. As discussed elsewhere herein, each operation module that is being adapted by artificial intelligence receives appropriate data inputs for the artificial intelligence operations that are performing the adaptive optimizations. For example, for artificial intelligence that adapts a user interface interactions may receive, as input, data indicative of operator answers/choices when presented with different user interface options. As another example, artificial intelligence that optimizes dialyzer transfer efficiently may receive, as input, the rate of dialyzer urea clearance.

Following the step 604 is a step 606 where the system uses artificial intelligence to adapt operational parameters according to the input data received. Generally, the specific adaptive optimizations that occur depend upon the input data, the artificial intelligence mechanism that is used (e.g., neural networks), and the specific objective of the artificial intelligence adaptive optimizations (e.g., optimize dialyzer transfer efficiently). Following the step 606 is a test step 608 where it is determined if the state of the module is acceptable after the adaptive optimizations have been applied at the step 606. Although adaptive optimizations using artificial intelligence may be useful, it is important that the adaptive optimizations do not cause the system to operate in a way that is potentially unsafe for patients or otherwise detrimental. This is enforced by a supervisor module, which is discussed in more detail elsewhere herein.

If it is determined at the step 608 that the new state of the module is not acceptable, then control transfers from the test step 608 to a step 612 where the state of the module is restored/reverted to a previous state. The previous state may be either an initial state (i.e., the state set at the step 602, described above), the state of the module just prior to execution of the step 606, or some other state that is otherwise acceptable. The previous state may be an original validated state. Following the step 612, control transfers back to the step 604 for another iteration. Note that the step 604 also follows directly from the step 608 if it determined at the step 608 that the state of the operation module is acceptable.

Figure 7:
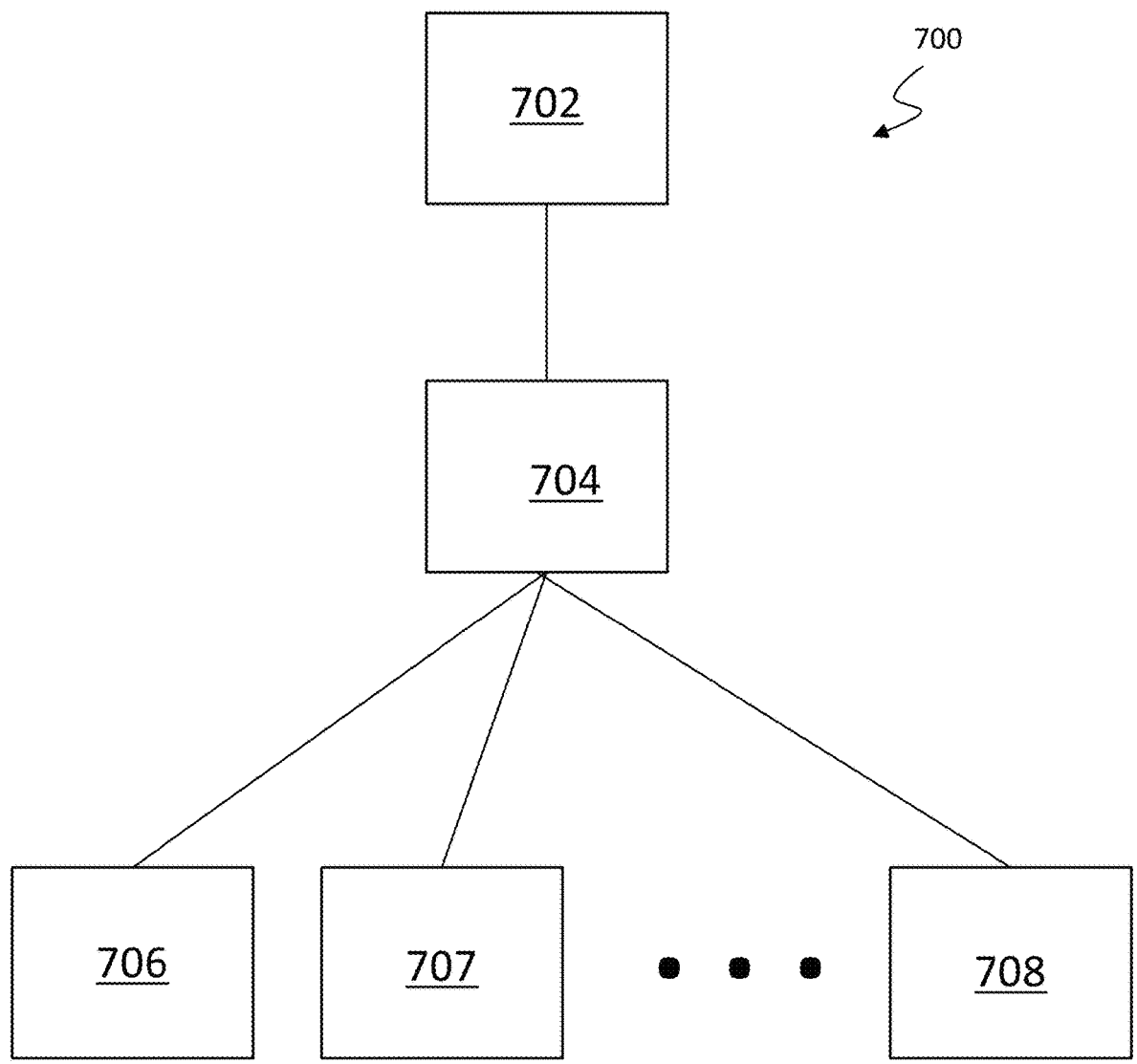
FIG. 7 is a schematic diagram showing a factory module, a supervisor module, and a plurality of operation modules according to an embodiment of the system described herein.

Referring to FIG. 7, a diagram 700 illustrates a relationship between a factory module 702, a supervisor module 704, and a plurality of operation modules 706-708. The supervisor module 704 and the operation modules 706-708 are provided on a dialysis system, such as the hemodialysis system 100 or the PD system 200, while the factory module 702 is external to the dialysis system and may be provided at the point of manufacture of the dialysis system or may possibly be provided in connection with maintenance of the dialysis system. As described in more detail elsewhere herein, the factory module 702 provides, in a secure and non-repudiable manor, limits/constraints to the supervisor module 704 that the supervisor module 704 uses to provide limits/constraints in a secure and non-repudiable manor to adaptive optimizations/state changes to each of the operation modules 706-708.

As discussed elsewhere herein, the operation modules 706-708 may include hardware and software portions of the dialysis system that control one or more of: operator user interface interactions with the system, auto calibration functions, automatic system noise reduction and compensation (electrical and mechanical), data transport, total time of dialysis and changeover, hardware and software operations, housekeeping, fault monitoring, and related response management, diagnostics, field service responses, etc. The supervisor module 704 constrains adaptive optimizations of the operation modules 706-708 provided by artificial intelligence to maintain each of the operation modules 706-708 in a state that is consistent with operating in a safe and effective manner and consistent with prior regulatory approval for each of the modules 706-708. The supervisor module 704 handles the test at the step 608, discussed above, where it is determined if the state of a particular operation module is acceptable after having been altered using artificial intelligence.

In an embodiment herein, a set of constraints for the operation modules may be determined when a dialysis system is manufactured (or some time after manufacture in connection with maintenance). Note that it is possible for different specific units of the same model of dialysis system to use different constraints due to calibration differences and/or possibly different deployment scenarios. The factory module 702 provides constraint data to the supervisor module 704 and provides a cryptographic one-way hash of the constraint data. In an embodiment herein, the cryptographic one-way hash is an SHA256 hash, although any appropriate cryptographic one-way hash may be used. The factory module 702 may also have a private/public cryptographic key pair and may provide the public key to the supervisor module 704. In an embodiment herein, the public key may be provided in a digital certificate that is signed by a trusted authority under the X.509 PKI standard. The factory module 702 may then provide to the supervisor module 704 a digital signature of the cryptographic one-way hash of the constraint data. The supervisor module 704 may then verify the source of the digitally-signed cryptographic one-way hash of the constraint data using the public key of the factory module 702 and may then authenticate the received constraint data using the one-way hash value. Note that this mechanism prevents repudiation of the constraint data since the only possible source is the factory module 702, assuming that the private key has not been disclosed to any party outside the factory module 702.

Figure 8:
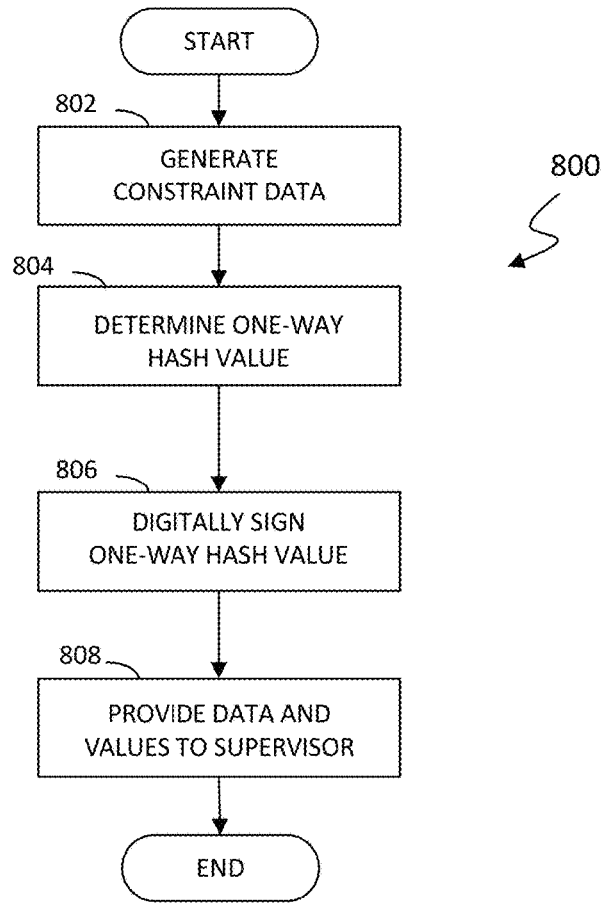
FIG. 8 is a flow diagram illustrating processing performed in connection with transferring state constraint data from a factory module to a supervisor module according to an embodiment of the system described herein.

Referring to FIG. 8, a flow diagram 800 illustrates steps performed by the factory module 702 in connection with providing the constraint data to the supervisor module. Processing begins at a first step 802 where the factory module 702 determines the constraint data. Generally, constraints placed on a particular operation module are determined based on initial values used for the particular module as well as a determination of any limits needed for providing safe and effective treatment. Some of the constraints may be determined empirically based on clinical experience. It is also possible for some of the constraints to be based, at least in part, on regulatory considerations, where values of some operational parameters are not allowed to go beyond values used for a particular operation module in connection with previously receiving regulatory approval.

Following the step 802 is a step 804 where a one-way hash value (e.g., SHA256) of the constraint data is calculated. Following the step 804 is a step 806 where the factory module 702 provides a digital signature of the one-way hash value. Following the step 806 is a step 808 where the factory module 702 provides the supervisor module with the constraint data, the one-way hash value of the constraint data, and the digital signature of the one-way hash value of the constraint data. Note that the processing illustrated by the flow diagram 800 may be performed when the dialysis system is first manufactured or in connection with subsequent maintenance after the dialysis system has been operational.

It is also possible for the supervisor module 704 to have a private key and a corresponding public key that may be used for the secure and non-repudiable transfer of data to the operation modules 706-708. Just as with transfer of data from the factory module 702 to the supervisor module 704, data from the supervisor module 704 may be transferred to each of the operation modules 706-708 by first determining a one-way has of the data (using, for example, the SHA256 one-way cryptographic hash mechanism), digitally signing the one-way hash value, and then transferring the data, the one-way hash value, and the digital signature of the one-way hash value. Similarly, each of the operation modules 706-708 may have a private key and a corresponding public key that may be used to provide a secure and non-repudiable data transfer to the supervisor module 704. Transferring data between the supervisor module 704 and the operation modules 706-708 in connection with determining if a new state of the operation module is acceptable (the test step 608 in the flow diagram 600, discussed above) and in connection with restoring/reverting the state of a module (the step 612 in the flow diagram 600, discussed above) is discussed in more detail elsewhere herein.

Figure 9:
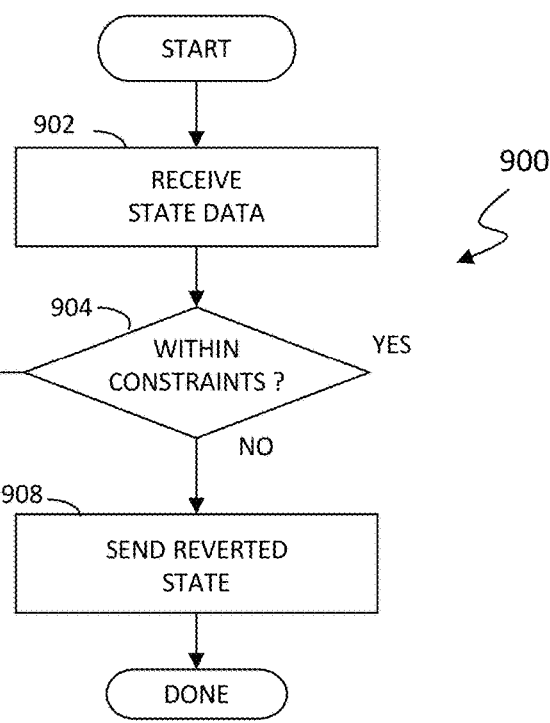
FIG. 9 is a flow diagram illustrating processing performed in connection with a supervisor module handing state change of an operation module according to an embodiment of the system described herein.

Referring to FIG. 9, a flow diagram 900 illustrates processing performed in connection with the supervisor module 704 determining if a new state of an operation module is acceptable and restoring/reverting a state of the operation module if the new state is not acceptable. Processing begins at a first step 902 where the supervisor module 704 receives state data for the new state from the operation module being tested (i.e., one of the operation modules 706-708). In an embodiment herein, the state data is provided along with a one-way has value of the state data (using, for example, SHA256) and a digital signature of the one-way hash value. Note that providing the data along with the one-way hash value and the digital signature renders the data secure and non-reputable. In some embodiments, the supervisor module 704 may store the state data (for archival purposes) and may perform a one-way hash (e.g., SHA256) on the data and digitally sign the one-way hash. The non-repudiable snapshots of the data may be useful for subsequent diagnostics or as proof of a particular operational state.

Following the step 902 is a test step 904 where the security module 704 examines the state data to determine if any of the operational parameters of the new state are outside any constraints that were provided as part of the constraint data previously transferred from the factory module 702 to the security module 704, as described elsewhere herein. If none of the new operational parameters are outside any of the constraints, then control transfers from the step 904 to a step 906 where a confirmation is sent from the supervisor module 704 to the operation module being tested. Receipt of the confirmation causes the operation module to begin operating in the new state. Following the step 906, processing is complete. If it is determined at the test step 904 that at least one of the new operational parameters are outside the constraints, then control transfers from the step 904 to a step 908 where a data for a previous state is sent to the operation module to cause the operation module to revert to the previous state. Following the step 906, processing is complete. The previous state may be either an initial state, the state of the operation module just prior to determining the new state, or some other previous state that is acceptable. Generally, the previous state is a prior validated state. Following the step 908, processing is complete.

Figure 10:
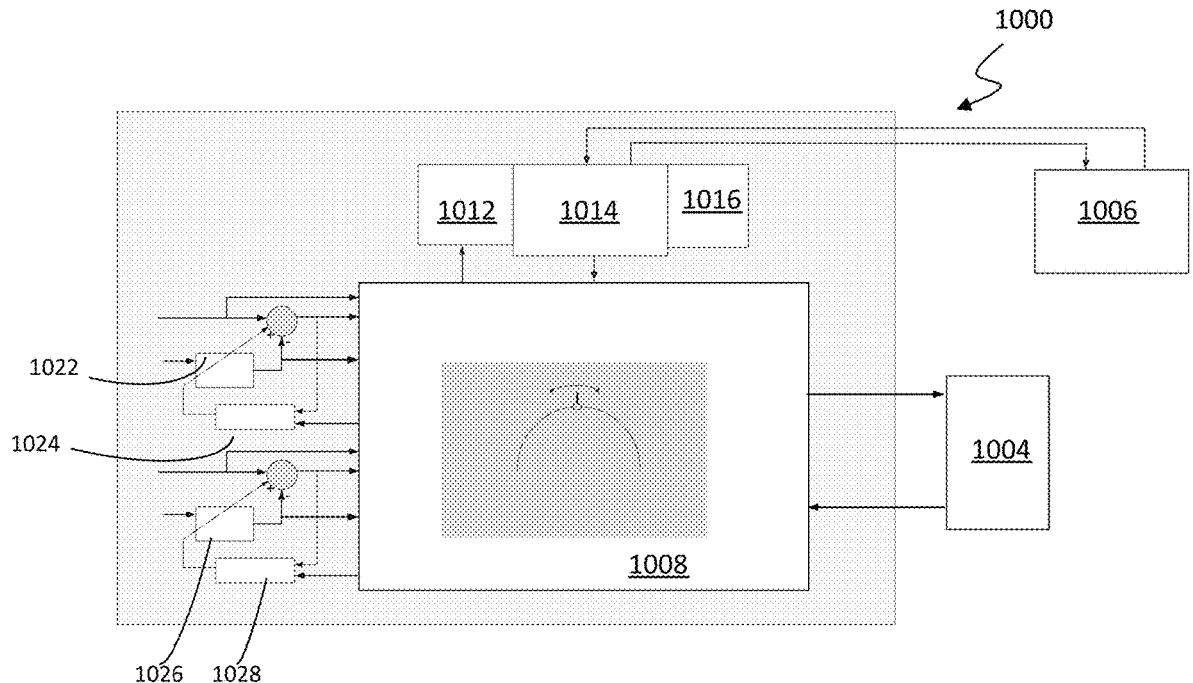
FIG. 10 is a schematic diagram showing a dialysis system, a factory acceptance test system, artificial intelligence based optimization algorithms, an authentication and supervisory engine, a dynamic operational data set, and a static operational data set according to an embodiment of the system described herein.

Referring to FIG. 10, a diagram 1000 shows a dialysis system 1002 coupled to a patient/nurse/doctor 1004 that provides input to and receives output from the dialysis system 1002. The dialysis system 1002 may also be coupled to a factory acceptance test system 1006 that provides baseline data and constraints, as described in more detail elsewhere herein. Note that the factory acceptance test system 1006 may be coupled to the dialysis system intermittently and used, for example, when the dialysis system 1002 is manufactured and when the dialysis system 1002 is maintained after the date of manufacture. In some embodiments, the factory acceptance test system 1006 is not usually present during operation of the dialysis system 1002 with patients.

The dialysis system 1002 includes one or more artificial intelligence based optimization algorithms 1008 that provide data to a dynamic operational data set 1012 and receive data from an authentication and supervisory engine 1014. The authentication and supervisory engine 1014 contains mechanisms for constraining critical parameters, as described elsewhere herein, and may include a control value table, a guard/compliance enforcer, AI specific learning rules, and mechanisms for handling loading and monitoring of dynamic system baseline data. The authentication and supervisory engine 1014 exchanges data with the factory acceptance test system 1006 when the factory acceptance test system 1006 is present. The authentication and supervisory engine 1014 also receives data from a static operational data set 1016. The static operational data set 1016 includes static (fixed) counterparts for data provided by the dynamic operational data set 1012. In an embodiment herein, both the dynamic operational data set 1012 and the static operational data set 1016 contain static and dynamic corresponding data for system specific operating parameters, system calibration data, system configuration data, system alarm limits and safe operating limits, and embedded processor/FPGA boot code. The factory acceptance test system 1006 provides authentication and facilitates copying data from the static operational data set 1016 to the authentication and supervisory engine 1014.

The artificial intelligence based optimization algorithms 1008 exchange data with a first adaptive control algorithm 1022 and a corresponding first adaptive correction algorithm 1024 and exchange data with a second adaptive control algorithm 1026 and a corresponding second adaptive correction algorithm 1028. By way of example, the first adaptive control algorithm 1022 may receive as input 6F, a flow rate parameter representing a change of flow rate, and the first adaptive correction algorithm 1024 may receive as input 6P, a flow rate control parameter. In a dialysis system, it is desirable to optimize (maximize) KUF, the ultrafiltration coefficient of the dialyzer, which is given by:

$$KUF = V/(T \times P)$$

where V is an amount of fluid crossing a membrane of the dialyzer (in ml), T is time (in hours), and P is pressure (in mm Hg). The first adaptive control algorithm 1022 and the first adaptive correction algorithm 1024 may perform this optimization using any one of a number of possible mechanisms, including known optimization mechanisms. However, for safety/regulatory considerations, a corresponding one of the artificial intelligence based optimization algorithms 1008 is constrained by the authentication and supervisory engine 1014 to prevent operational parameters from deviating too far from values of the static operational data set 1016.

Note that, in a similar way, the second adaptive control algorithm 1026 and the corresponding second adaptive correction algorithm 1028 may be used to optimize other operational parameters, such as a fluid pressure difference exerted across the dialyzer membrane.

Figure 11:
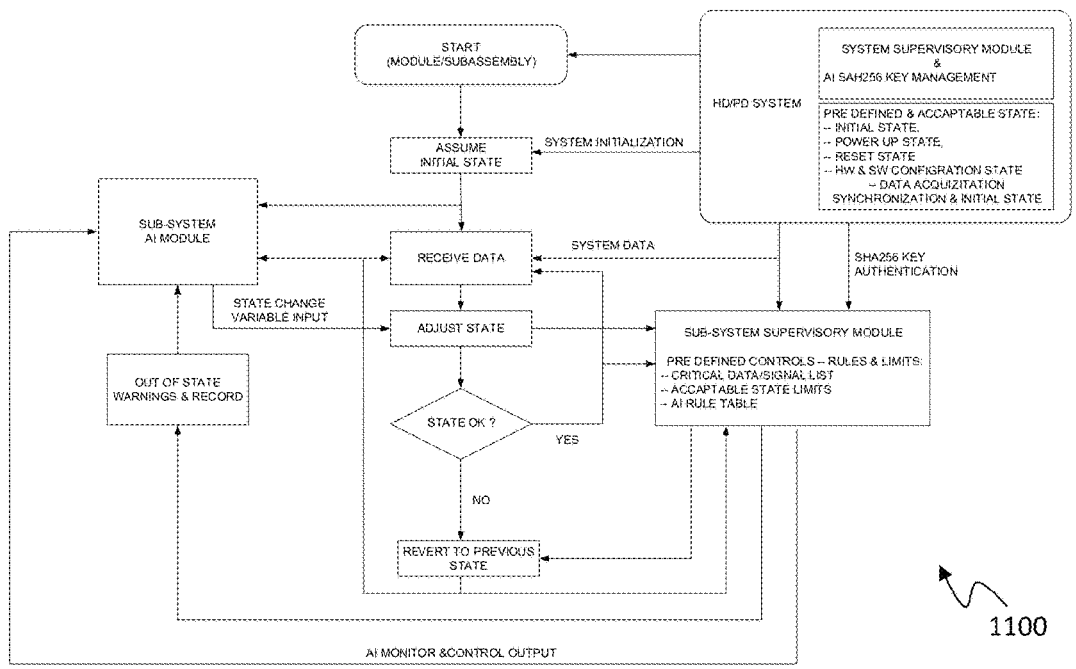
FIG. 11 is a schematic diagram illustrating flow between different components according to an embodiment of the system described herein.

Referring to FIG. 11, a schematic diagram 1100 illustrates flow between different components of the system described herein. More specifically, the diagram 1100 indicates an interaction of an AI module with Supervisory modules in a process flow and shows how the modules are linked and connected and how the modules interact with other modules. The diagram 1100 also illustrates how process/operational variables interact with the AI and Supervisory modules. Note that a similar flow may be applied to each AI implemented subassembly/module.

Although an example processing system has been described in FIG. 5, implementations of the subject matter and the functional operations described above may be implemented in other types of digital electronic circuitry, or in computer software, firmware, or hardware, including the structures disclosed in this specification and their structural equivalents, or in combinations of one or more of them. Implementations of the subject matter described in this specification may be implemented as one or more computer program products, i.e., one or more modules of computer program instructions encoded on a tangible program carrier, for example a computer-readable medium, for execution by, or to control the operation of, a processing system. The computer readable medium may be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system may include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) may be written in any form of programming language, including compiled or interpreted languages, or declarative or procedural languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory may be supplemented by, or incorporated in, special purpose logic circuitry. The components of the system may be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed is:

1. A method of constraining adaptive optimizations of operational parameters of an operation module of a medical device, comprising:
    determining if a new state corresponding to an adjustment of values of at least one of the operational parameters results in at least one of the operational parameters being outside at least one of a plurality of constraints that have been provided to the medical device, the constraints being non-repudiable;
    accepting the new state if none of the operational parameters are outside any of the constraints; and
    reverting the medical device to a previous valid state if at least one of the operational parameters is outside at least one of the constraints, wherein the constraints are provided to the medical device along with a one-way hash value of the constraints that is digitally signed.

2. A method, according to claim 1, wherein the adaptive optimizations vary based on relevant inputs to an artificial intelligence module and on specific objectives of the adaptive optimizations.

3. A method, according to claim 1, wherein the medical device is a dialysis system.

4. A method, according to claim 1, wherein the one-way hash value of the constraints is a SHA256 hash value.

5. A method, according to claim 1, wherein the one-way hash value of the constraints is digitally signed using a private key that is part of a public key/private key pair.

6. A method, according to claim 1, wherein the medical device is provided in an initial state prior to any adaptive optimizations according to one of: an operator of the system or a patient receiving treatment from the medical device.

7. A method, according to claim 6, wherein either the operator or the patient is detected automatically by the medical device.

8. A method, according to claim 1, wherein an operation module that stores state data provides the state data to a supervisor module that determines if the new state has at least one operational parameter that is outside a constraint based on state data provided by the operation module and wherein the supervisor module reverts the operation module to a previous state if at least one operational parameter is outside a constraint.

9. A method, according to claim 8, wherein a digitally signed one way hash value of the state data is provided by the operation module.

10. A dialysis system, comprising:
a dialysis machine; and
a control unit having a processor that executes software in a non-transitory computer readable medium, the software operating the dialysis machine and constraining adaptive optimizations of operational parameters of the dialysis system, the software including executable code that determines if a new state corresponding to an adjustment of values of at least one of the operational parameters results in at least one of the operational parameters being outside at least one of a plurality of constraints that have been provided to the dialysis machine, the constraints being non-repudiable, executable code that accepts the new state if none of the operational parameters are outside any of the constraints, and executable code that reverts the medical device to a previous valid state if at least one of the operational parameters is outside at least one of the constraints, wherein the constraints are provided to the dialysis machine along with a one-way hash value of the constraints that is digitally signed.

11. A dialysis system, according to claim 10, wherein the adaptive optimizations vary based on relevant inputs to an artificial intelligence module and on specific objectives of the adaptive optimizations.

12. A dialysis system, according to claim 10, wherein the one-way hash value is a SHA256 hash value.

13. A dialysis system, according to claim 10, wherein the control unit further includes an operation module that stores state data and a supervisor module that receives the state data from the operation module and determines if the new state has at least one operational parameter that is outside a constraint based on state data provided by the operation module.

14. A dialysis system, according to claim 13, wherein the supervisor module reverts the operation module to a previous state if at least one operational parameter is outside a constraint.

15. A dialysis system, according to claim 13, wherein a digitally signed one way hash value of the state data is provided by the operation module.

16. A dialysis system, according to claim 10, wherein the one-way hash value of the constraints is digitally signed using a private key that is part of a public key/private key pair.

17. A dialysis system, according to claim 10, wherein the dialysis system is provided in an initial state prior to any adaptive optimizations according to one of: an operator of the system or a patient receiving treatment from the dialysis machine.

18. A dialysis system, according to claim 17, wherein either the operator or the patient is detected automatically by the dialysis machine.

* * * * *